United States Patent [19]
Konishi et al.

[11] Patent Number: 5,916,918
[45] Date of Patent: Jun. 29, 1999

[54] METHOD FOR TREATING A SKIN INJURY COMPRISING TOPICALLY APPLYING ACETYLSALICYLIC ACID

[75] Inventors: Ryoji Konishi; Mitsuhiro Kawada; Noriko Mizobuchi; Sayuri Seto, all of Kagawa-ken; Osamu Hatase; Masaaki Tokuda, both of Takamatsu, all of Japan

[73] Assignee: Teikoku Seiyaku Kabushiki Kaisha, Kagawa-ken, Japan

[21] Appl. No.: 08/772,845

[22] Filed: Dec. 24, 1996

[30] Foreign Application Priority Data

Dec. 26, 1995 [JP] Japan ................................. 7-338745

[51] Int. Cl.⁶ ................................................. A61K 31/22
[52] U.S. Cl. ........................................... 514/546; 514/928
[58] Field of Search ............................................. 514/546

[56] References Cited

U.S. PATENT DOCUMENTS 3,341,410  9/1967  Ochs .
3,842,170  10/1974  Luzzi et al. .

FOREIGN PATENT DOCUMENTS 55635     7/1982   European Pat. Off. .
146847    7/1995   European Pat. Off. .
2307522   11/1976  France .
4241128   6/1993   Germany .

OTHER PUBLICATIONS

Facts and Comparisons, Sewester et al 1990.
WPIDS AN 95–340179, Sep. 5, 1995.
Enbase AN 96009688, Smith 1995.
HCA Plus 124:37522, Franke et al 1995.
Biosis AN 95: 490422, Steen et al 1995.
"Vidal" 1993, Editions Du Vidal, Paris, France XP002030528, Aspirine du Rhone 500, p. 117.
*European Journal of Pharmacology,* vol. 183, No. 6, 1990, pp. 2271–2272, XP000653454, Corss et al., "The pharmacological modification of wound healing: a quantitative approach."

*Primary Examiner*—Rebecca Cook
*Attorney, Agent, or Firm*—Birch, Stewart, Kolasch & Birch, LLP

[57] ABSTRACT

A drug for the treatment of skin injuries, particularly hardly curable diseases such as bedsore, which comprises as an active ingredient acetylsalicylic acid. The drug is used in the form of a topical preparation for external application or is administered orally to the patients.

8 Claims, 5 Drawing Sheets

METHOD FOR TREATING A SKIN INJURY COMPRISING TOPICALLY APPLYING ACETYLSALICYLIC ACID

FIELD OF INVENTION

This invention relates to new medical use of acetylsalicylic acid, that is, a drug for the treatment of skin injuries which comprises as an active ingredient acetylsalicylic acid.

PRIOR ART

Acetylsalicylic acid is well known in the tradename of "Aspirin" and has widely been used as a drug for the treatment of head ache, etc. by its potent analgesic activity with mild antipyretic and antireumatic activities. On the other hand, this compound may occasionally induce digestive ulcer or aspirin asthma by administration for a long period of time, and in fact, an ulcer induced by aspirin in an experimental animal has widely been used as an experimental model for gastric ulcer. Besides, many salicylic acid derivatives have anti-inflammatory and analgesic activities and hence have been used as an external drug for the treatment of bruise, sprain, etc. Thus, acetylsalicylic acid has widely been used in medication, but it has never been used for the treatment of wound.

Skin injury is a wound of the skin and is mainly caused by physical factors (e.g. ambustion, abrasion, laceration). The treatment of such skin injuries has mainly been effected by nosotropic treatment. For example, in case of bedsores which are one of the hardly curable diseases, and attention has been given to develop a useful method for the treatment thereof bedsores are now treated merely by employing means for removal of cause for occurrence of bedsore, or by washing, cleaning or sterilizing the wound surface, or by arranging the conditions for forming granulation tissue and epidermal tissue on the wound surface. There is known a drug for promoting positively the formation of granulation tissue or epidermal tissue, such as an extract from hemolysed blood of young cattle (a tradename, Sorcoseryl), Bucladesine Sodium, Tretinoin Tocoferil, but these commercially available drugs do not necessarily exhibit sufficient therapeutic effects and hence the injuries are not completely remedied in most patients. Accordingly, it has been desired to develop a new medicament which has potent activities against skin injuries and is well effective on such hardly curable diseases such as bedsores.

BRIEF SUMMARY OF THE INVENTION

Under the circumstances, the present inventors have intensively investigated a new medicament which can significantly promotes the formation of epidermal tissue and have found that acetylsalicylic acid is suitable for said purpose.

That is, the present inventors have tried to apply a topical preparation containing acetylsalicylic acid in a concentration of 0.1 to 10% by weight to an injured region of skin, specifically in a rat model of bedsore and a rat model of ambustion and burn, and have found that it showed remarkable remedy of the injured tissues in those injuries and inhibited the formation of crust even in a deep skin injury as reached to the muscular layer but instead promoted the formation of granulation tissue and epidermal tissue. Besides, it has been found that when acetylsalicylic acid was orally administered in an amount of 15–75 mg/kg/day to a rat skin-deficient model, it showed the same or similar effects as the above-mentioned topical preparation.

Moreover, it has also been found that when the above topical preparation was applied to a hardly curable bedsore in human patients, there have been observed remarkable reduction of injured area and remedy of wound in all patients. In the treatment of ambustion and burn, it showed remarkable recovery of skin injuries in addition to the known analgesic effects of acetylsalicylic acid. The therapeutic effects will be expected in every skin injuries.

Thus, an object of the present invention is to provide a new drug for the treatment of skin injuries which comprises as an active ingredient acetylsalicylic acid. Another object of the invention is to provide a topical preparation for the treatment of skin injuries which comprises as an active ingredient acetylsalicylic acid and a conventional pharmaceutically acceptable carrier or diluent. A further object of the invention is to provide a method for the treatment of skin injuries, especially hardly curable injuries such as bedsore by applying a topical preparation comprising acetylsalicylic acid to the injured region of skin or by administering orally a drug comprising acetylsalicylic acid. These and other objects of the invention will be apparent to those skilled in the art from the following description.

DETAILED DESCRIPTION OF THE INVENTION

Figure 1:
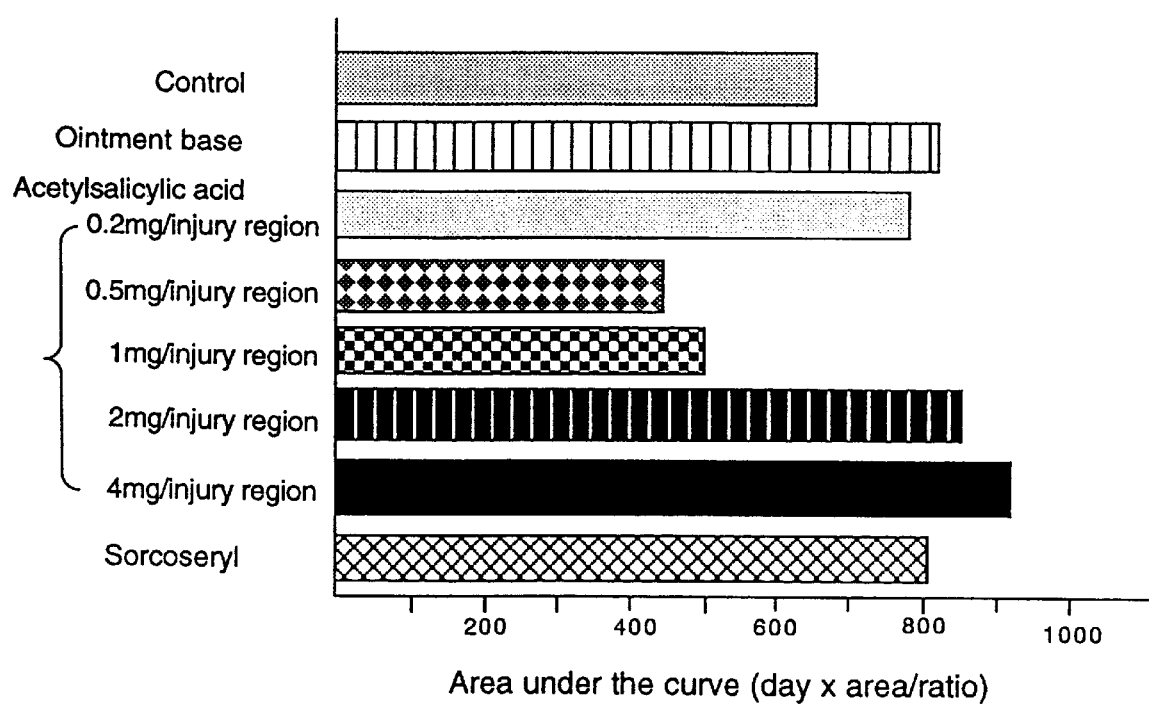
FIG. 1 shows a graph exhibiting therapeutic effects of acetylsalicylic acid when topically applied to a rat experimental bedsore model.

The drug for the treatment of skin injuries of the present invention may be in the form of a preparation suitable for topical application, or a preparation suitable for oral administration.

The activity of the acetylsalicylic acid depends on the concentration thereof in the preparation, and when the concentration thereof is over 15% by weight, it affects rather badly on the skin injuries, and when the concentration is less than 0.05% by weight, it can not exhibit its therapeutic effects. Accordingly, the topical preparation of the present invention contains 0.05 to 15% by weight, preferably 0.1 to 10% by weight, more preferably 0.2 to 8% by weight, of acetylsalicylic acid based on the whole weight of the preparation.

When the preparation of the present invention is administered orally, the effects of the active ingredient is also depended on the dosage thereof, and when the dose of acetylsalicylic acid is too high, it rather affects badly on the injuries, and when the dose thereof is too low, it does not exhibit the desired effects. Thus, when it is orally administered, it is used in a dose of 15–75 mg/kg per day, preferably 20–65 mg/kg per day, more preferably 30–60 mg/kg per day.

The preparation for the treatment of skin injuries of the present invention may be formulated in any conventional preparation for topical application, such as ointment, cream, gel, gel ointment, plaster (e.g. cataplasm, poultice), solution, powders, and the like. These preparations may be prepared by a conventional method with conventional pharmaceutically acceptable carriers or diluents as mentioned below.

For example, in the preparation of an ointment, vaseline, higher alcohols, beeswax, vegetable oils, polyethylene glycol, etc. are used. It is convenient to use commercially available ointment bases such as "Plastibase".

In the preparation of a cream preparation, fats and oils, waxes, higher fatty acids, higher alcohols, fatty acid esters, purified water, emulsifying agents etc. are used.

In the preparation of gel preparation, conventional gelling materials such as polyacrylates (e.g. sodium polyacrylate), hydroxypropyl cellulose, hydroxypropyl methyl cellulose, polyvinyl alcohol, polyvinylpyrrolidone, purified water, lower alcohols, polyhydric alcohols, polyethylene glycol, and the like are used.

In the preparation of a gel ointment preparation, an emulsifying agent (preferably nonionic surfactants), an oily substance (e.g. liquid paraffin), etc. are used in addition to the gelling materials as mentioned above.

The plaster such as cataplasm or poultice can be prepared by spreading a gel preparation as mentioned above onto a support (e.g. fabrics, non-woven fabrics).

In addition to the above-mentioned ingredients, paraffines, squalane, lanolin, cholesterol esters, higher fatty acid esters, and the like may optionally be used. Moreover, any antioxidants such as BHA, BHT, propyl gallate, pyrogallol, tocopherol, etc. may also be incorporated.

In addition to the above-mentioned preparations and components, there may optionally be used any other conventional formulations for dermatologic preparations or be incorporated with any other additives. Besides, the dermatologic preparations may be prepared by any other conventional methods or formulations.

The drug for the treatment of skin injuries of the present invention may also be in the preparation suitable for oral administration such as tablets, pills, powders, granules, fine granules, capsules, dry syrups, etc. These preparations for oral administration can be prepared by a conventional method with conventional pharmaceutically acceptable carriers or diluents, such as fillers, thickening agents, binders, wetting agents, disintegrators, surfactants, lubricants, and the like.

In order to form in tablets, there are used conventional pharmaceutically acceptable carriers such as vehicles (e.g. lactose, white sugar, starches, calcium carbonate, kaolin, crystalline cellulose, etc.), binders (e.g. water, simple syrup, glucose solution, starch solution, gelatin solution, carboxymethyl cellulose, shellac, methyl cellulose, polyvinylpyrrolidone, etc.), disintegrators (e.g. dry starch, sodium arginate, agar powder, carmellose, polyoxyethylene sorbitan fatty acid esters, sodium laurylsulfate, stearic monoglyceride, etc.), disintegration inhibitors (e.g. white sugar, stearin, cacao butter, hydrogenated oils, etc.), wetting agents (e.g. glycerin, propylene glycol, etc.), adsorbents (starches, lactose, bentonite, colloidal silicates, etc.), lubricants (e.g. purified talc, stearates, calcium sulfate, etc.), and the like. Moreover, the tablets may also be in the form of a conventional coated tablet, such as sugar-coated tablets, gelatin-coated tablets, enteric coated tablets, film coating tablets, or double or multiple layer tablets.

In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, cetanol, etc.), disintegrators (e.g. carmellose, agar, etc.), and the like.

Granules and fine granules can be prepared by mixing the active compound with vehicles, binders and the like as mentioned above and granulating or fine granulating the mixture in a usual manner.

Capsules can be prepared by charging a mixture of acetylsalicylic acid with the above-mentioned carriers, preferably in the form of granules, fine granules, powders, into hard gelatin capsules or soft capsules in a usual manner.

In these preparations for oral administation, the content of the active acetylsalicylic acid may vary depending on the forms of preparation, and in case of solid preparations such as tablets, granules, fine granules, or powders, it is usually contained in an amount of 30 to 70% by weight, preferably 40 to 60% by weight, based on the whole weight of the preparation; and in case of liquid preparations such as syrup, it is usually contained in an amount of 0.1 to 10% by weight, preferably 0.5 to 5% by weight, based on the whole weight of the preparation.

The present invention is illustrated by the following Examples and Experiments but should not be construed to be limited thereto.

EXAMPLE 1

An ointment is prepared with the following formulation by the steps of dissolving acetylsalicylic acid in a small amount of ethanol, evaporating the solvent to give fine powders, mixing uniformly the fine powders with a surfactant (Tween 80), adding the resulting mixture to an ointment base ("Plastibase"), and finally mixing them well.

| Components | Amounts |
| --- | --- |
| Acetylsalicylic acid | 0.5 g |
| Tween 80 (polysorbate 80) | 5.0 g |
| Plastibase | 94.5 g |
| Ethanol | A slight amount |

EXAMPLE 2

An ointment is prepared with the following formulation in the same manner as described in Example 1.

| Components | Amounts |
| --- | --- |
| Acetylsalicylic acid | 1.0 g |
| Tween 80 | 5.0 g |
| Plastibase | 94.5 g |
| Ethanol | A slight amount |

EXAMPLE 3

An ointment is prepared with the following formulation in the same manner as described in Example 1.

| Components | Amounts |
| --- | --- |
| Acetylsalicylic acid | 2.0 g |
| Tween 80 | 5.0 g |
| Plastibase | 93.0 g |
| Ethanol | A slight amount |

EXAMPLE 4

An ointment is prepared with the following formulation in the same manner as described in Example 1.

| Components | Amounts |
| --- | --- |
| Acetylsalicylic acid | 0.5 g |
| Span 30 (Sorbitan sesquioleate) | 5.0 g |
| White vaseline | 94.5 g |
| Ethanol | A slight amount |

EXAMPLE 5

An ointment is prepared with the following formulation in the same manner as described in Example 1.

| Components | Amounts |
| --- | --- |
| Acetylsalicylic acid | 1.0 g |
| HCO-60 (Polyoxyethylene hydrogenated caster oil) | 5.0 g |
| Plastibase | 94.0 g |
| Ethanol | A slight amount |

EXAMPLE 6

An ointment is prepared with the following formulation in the same manner as described in Example 1.

| Components | Amounts |
| --- | --- |
| Acetylsalicylic acid | 2.0 g |
| HCO-60 | 5.0 g |
| White vaseline | 93.0 g |
| Ethano 1 | A slight amount |

EXAMPLE 7

An ointment is prepared with the following formulation in the same manner as described in Example 1.

| Components | Amounts |
| --- | --- |
| Acetylsalicylic acid | 15.0 g |
| Span 30 | 5.0 g |
| Plastibase | 80.0 g |
| Ethanol | A slight amount |

EXAMPLE 8

An ointment is prepared with the following formulation in the same manner as described in Example 1.

| Components | Amounts |
| --- | --- |
| Acetylsalicylic acid | 0.05 g |
| Tween 80 | 5.0 g |
| Plastibase | 94.95 g |
| Ethanol | A slight amount |

EXAMPLE 9

A plaster is prepared as follows. A gel preparation is prepared with the following formulation by the steps of dispersing uniformly sodium polyacrylate in glycerin, adding water thereto, mixing well the mixture until it becomes a transparent gelly material, and subsequently adding a homogeneous suspension of acetylsalicylic acid in propylene glycol to the above gelly material, mixing them with stirring, and further adding thereto a mixture of lactic acid in an aluminum hydroxide suspension, and finally mixing well the mixture with stirring. The gel preparation thus prepared is spread onto a fabric support, and the surface thereof is covered by a plastic film, and then the resultant is cut in an appropriate size to give the desired plaster.

| Components | Amounts |
| --- | --- |
| Sodium polyacrylic acid | 6.0 g |
| Propylene glycol | 10.0 g |
| Glycerin | 40.0 g |
| Aluminum hydroxide | 0.5 g |
| Lactic acid | 1.5 g |
| Acetylsalicylic acid | 1.0 g |
| Purified water | 41.0 g |

EXAMPLE 10

A plaster is prepared as follows. A gel preparation is prepared with the following formulation by the steps of dispersing uniformly sodium polyacrylate in glycerin, heating and then mixing well the mixture until it becomes a transparent gelly material, and subsequently adding a homogeneous suspension of acetylsalicylic acid in propylene glycol to the above gelly material, mixing them with stirring, and further adding thereto a homogeneous suspension of alum in glycerin, and finally mixing well the mixture with stirring. The gel preparation thus prepared is spread onto a fabric support, and the surface thereof is covered by a plastic film, and then the resultant is cut in an appropriate size to give the desired plaster.

| Components | Amounts |
| --- | --- |
| Sodium polyacryloate | 6.0 g |
| Propylene glycol | 10.0 g |
| Glycerin | 82.6 g |
| Acetylsalicylic acid | 1.0 g |
| Alum | 0.4 g |

EXAMPLE 11

Aspirin granules are prepared with the following formulation by the steps of mixing acetylsalicylic acid, crystalline cellulose and lactose, adding thereto a 10% aqueous solution of hydroxypropyl cellulose (54 g), kneading the mixture, and then granulating by extruding the kneaded mixture through a screen with holes (0.7 mmφ), drying, crushing and regulating the size in a usual manner.

| Components | Amounts |
| --- | --- |
| Acetylsalicylic acid | 100.0 g |
| Lactose | 36.0 g |
| Corn starch | 24.0 g |
| Crystalline cellulose | 34.6 g |
| Hydroxypropyl cellulose | 5.4 g |
| Purified water | 48.6 g |

EXAMPLE 12

Aspirin tablets are prepared by mixing the granules (490 g) as prepared in Example 11 with talc (10 g), and tableting the mixture with a tableting machine in a usual manner to give tablets (weight, 0.5 g per each tablet).

EXAMPLE 13

An aqueous preparation is prepared with the following formulation by the steps of dissolving acetylsalicylic acid in purified water, adding thereto simple syrup, and controling the whole content with purified water.

| Components | Amounts |
| --- | --- |
| Acetylsalicylic acid | 1.5 g |
| Simple syrup | 8.0 g |
| Purified water | q.s. |
| | Totally 100 ml |

EXAMPLE 14

An ointment is prepared with the following formulation by the steps of dissolving acetylsalicylic acid in a small amount of ethanol, evaporating the solvent to give fine powders, adding the fine powders to an ointment base (Plastibase), and finally mixing them homogeneously.

| Components | Amounts |
| --- | --- |
| Acetylsalicylic acid | 2.0 g |
| Plastibase | 98.0 g |
| Ethanol | A slight amount |

EXAMPLE 15

An ointment is prepared with the following formulation in the same manner as described in Example 14.

| Components | Amounts |
| --- | --- |
| Acetylsalicylic acid | 4.0 g |
| Plastibase | 96.0 g |
| Ethanol | A slight amount |

EXAMPLE 16

An ointment is prepared with the following formulation in the same manner as described in Example 14.

| Components | Amounts |
| --- | --- |
| Acetylsalicylic acid | 8.0 g |
| Plastibase | 92.0 g |
| Ethanol | A slight amount |

The suprior therapeutic effects of the drug comprising acetylsalicylic acid of the present invention are illustrated by the following experiments.

EXPERIMENT 1

Therapeutic effects of acetylsalicylic acid when topically applied to rat experimental bedsore model:

Wistar rats (weighing 400–450 g, 5 rats per group) were used. The rats (hair shaved at right femur) were anesthetized with pentobarbital, and the femur was pressed with a round pipe under a pressure of 1 kg/cm$^2$ for 6 hours per day for a period of 6 days to induce bedsore injury.

The test drug in the form of an ointment was applied to the rats from next day after the bedsore injury was induced in a dose of acetylsalicylic acid of 0.2 mg/injured region, 0.5 mg/injured region, 1 mg/injured region, 2 mg/injured region, or 4 mg/injured region, once a day for 14 days.

The therapeutic effects were evaluated by measuring the size in both of long and short diameters of the injured region to calculate the area, and then the change of area of injured region was calculated by the following equation:

$$\text{Change of area} = \frac{\text{Long diameter} \times \text{short diameter of injured region on the day observed}}{\text{Long diameter} \times \text{short diameter of injured region on the first day after inducing the injury}} \times 100$$

Based on the data thus calculated, a curve of the change of area was drawn, and the area below the curve was calculated. In the references, a commercially available "Solcoseryl" was used as an active ingredient, and the ointment base ("Plastibase") alone was applied.

The results are shown in FIG. 1. As is clear from FIG. 1, acetylsalicylic acid showed remarkable therapeutic effects in an amount of 0.5 mg/injured region and 1 mg/injured region.

EXPERIMENT 2

Therapeutic effects of acetylsalicylic acid when topically applied to rat experimental skin-deficient model:

Wistar rats (weighing 400–450 g, 6 rats per group) were used. The rats (hair shaved on the back, followed by sterilization) were anesthetized with ether, and the skin on the back was taken by a round punch (inner diameter, 12 mm) to induce injuries at two portions asymmetrically to the median line.

The test drug in the form of an ointment was applied to the rats from next day after the injury was induced in a dose of acetylsalicylic acid of 0.5 mg/injured region, 1 mg/injured region, or 2 mg/injured region, once a day for 14 days.

The therapeutic effects were evaluated by measuring the size in both of long and short diameters of the injured region to calculate the area. In the same manner as in Experiment 1, a curve of the change of area was drawn and the area below the curve was calculated. In the references, a commercially available "Solcoseryl" was used as an active ingredient, and the ointment base ("Plastibase") was applied.

Figure 2:
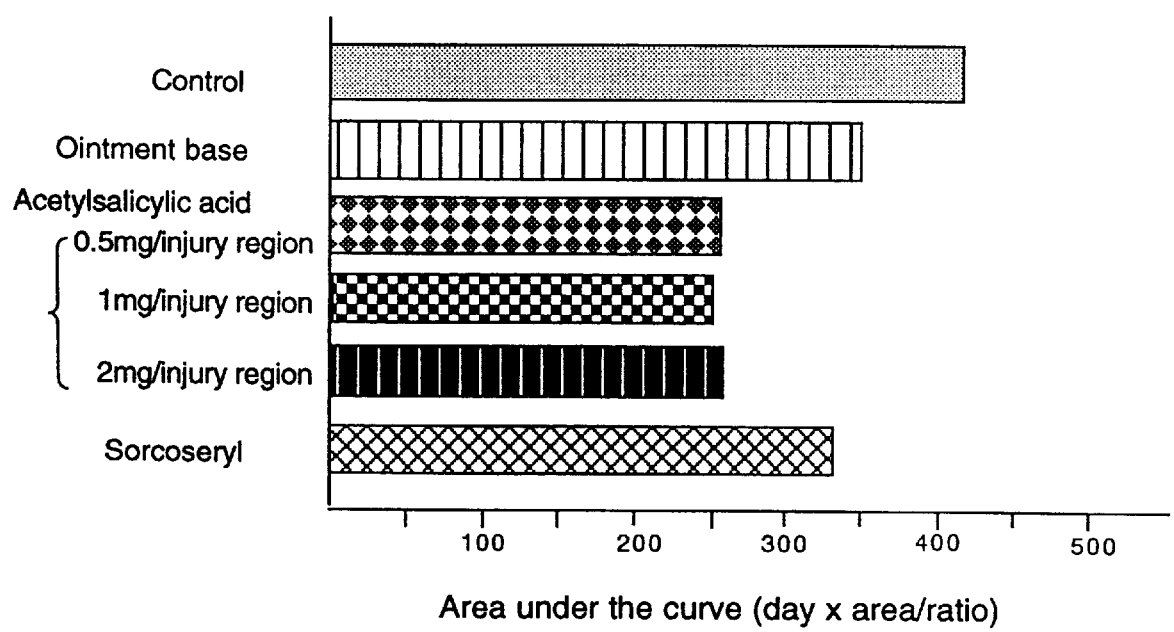
FIG. 2 shows a graph exhibiting therapeutic effects of acetylsalicylic acid when topically applied to a rat experimental skin-deficient model.

The results are shown in FIG. 2. As is clear from FIG. 2, acetylsalicylic acid showed remarkable therapeutic effects in an amount of 0.5 mg/injured region, 1 mg/injured region and 2 mg/injured region.

EXPERIMENT 3

Therapeutic effects of acetylsalicylic acid when topically applied to rat experimental ambustion model:

Wistar rats (weighing 400–450 g, 6 rats per group) were used. The rats (hair shaved on the back, followed by sterilization) were anesthetized with ether, and the skin on the back was contacted with a flatiron heated at 200° C. for 5 seconds to make ambustion.

The test drug in the form of an ointment was applied to the rats from next day after the injury was induced in a dose of acetylsalicylic acid of 1 mg/injured region or 2 mg/injured region, once a day for 17 days.

The therapeutic effects were evaluated by measuring the size in both of long and short diameters of the ambustion to calculate the area. In the same manner as in Experiment 1, a curve of the change of area was drawn and the area below the curve was calculated. In the references, a commercially available "Solcoseryl" was used as an active ingredient, and the ointment base ("Plastibase") alone was applied.

Figure 3:
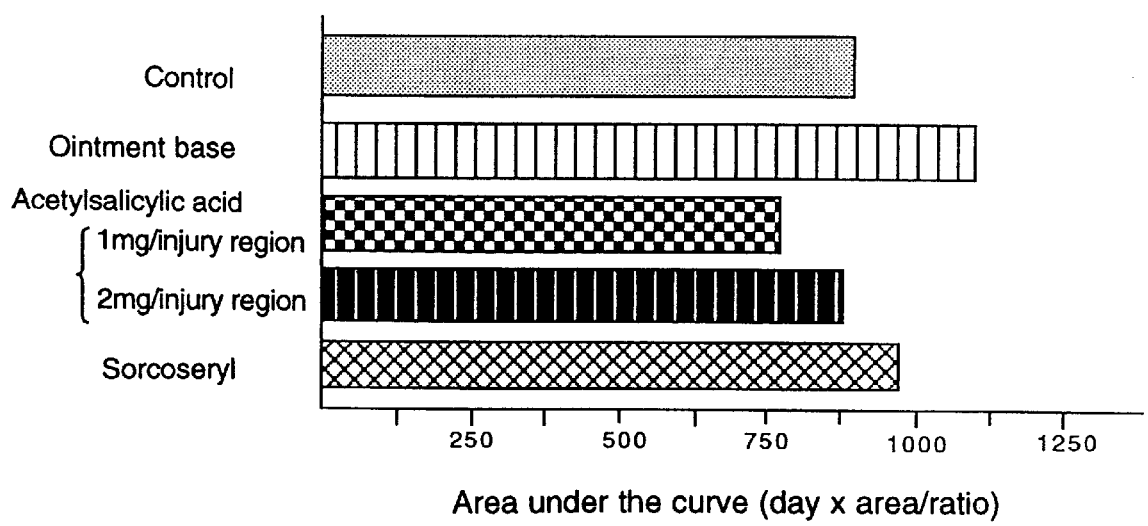
FIG. 3 shows a graph exhibiting therapeutic effects of acetylsalicylic acid when topically applied to a rat experimental ambustion model.

The results are shown in FIG. 3. As is clear from FIG. 3, acetylsalicylic acid showed remarkable therapeutic effects in an amount of 1 mg/injured region and 2 mg/injured region.

EXPERIMENT 4

Therapeutic effects of acetylsalicylic acid when administered orally to rat experimental skin-deficient model:

Wistar rats (weighing 400–450 g, 5 rats per group) were used. The rats (hair shaved on the back, followed by sterilization) were anesthetized with ether, and the skin on the back was taken by a round punch (inner diameter, 12 mm) to induced injuries at two portions asymmetrically to the median line.

Acetylsalicylic acid was orally administered to the rats from next day after the injury was induced in a dose of 15 mg/kg/day, 30 mg/kg/day, or 60 mg/kg/day, once a day for 13 days.

The therapeutic effects were evaluated by measuring the size in both of long and short diameters of the injured region to calculate the area. In the same manner as in Experiment 1, a curve of the change of area was drawn and the area below the curve was calculated.

Figure 4:
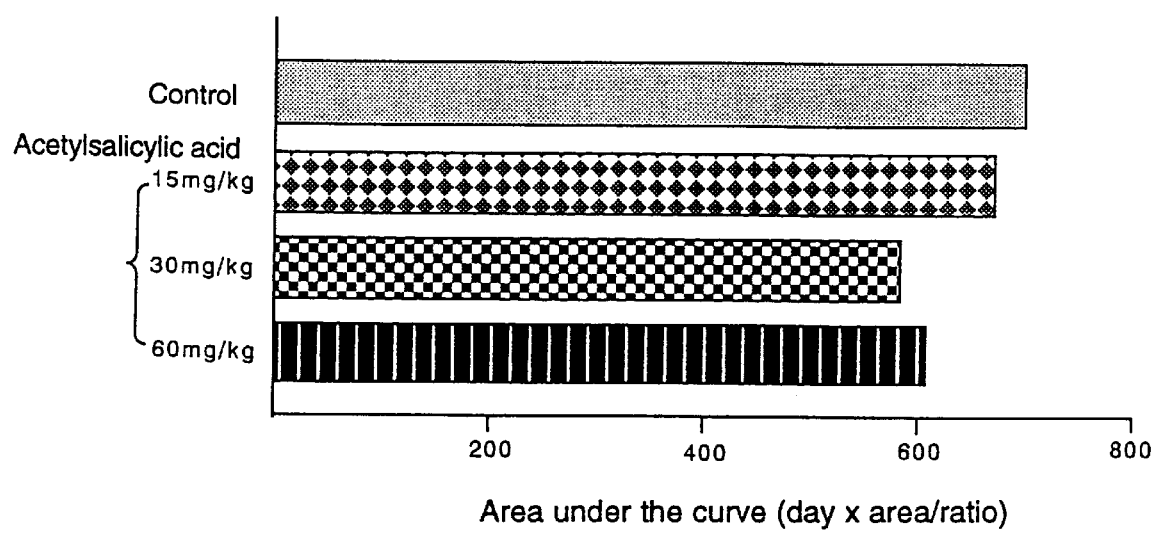
FIG. 4 shows a graph exhibiting therapeutic effects of acetylsalicylic acid when orally administered to a rat experimental skin-deficient model.

The results are shown in FIG. 4. As is clear from FIG. 4, acetylsalicylic acid showed remarkable therapeutic effects in a dose of 30 mg/kg/day and 6 mg/kg/day.

EXPERIMENT 5

Therapeutic effects on bedsore in human:

In order to test of therapeutic effects of acetylsalicylic acid on bedsore which is hardly cured by conventional drugs, an ointment containing 0.5% by weight of acetylsalicylic acid was applied to the injured region in 7 patients (totally 9 portions) for one or two weeks, and the effects were evaluated by four scores: "remarkably effective", "effective", "somewhat effective", and "not effective".

As a result, the test drug showed "remarkably effective" in 5 patients, "effective" in two patients, "somewhat effective" in one patient, and "not effective" in one patient. The patients who showed results of "somewhat effective" and "not effective" were suffered from very hardly curable bedsore with injury pocket. Thus, the ointment of this invention was effective for open type of wound.

EXPERIMENT 6

Therapeutic effects of acetylsalicylic acid when topically applied to rat experimental skin-deficient model:

Wistar rats (weighing 300–350 g, 5 rats per group) were used. The rats (hair shaved on the back, followed by sterilization) were anesthetized with ether, and the skin on the back was taken by a round punch (inner diameter, 10 mm) to induce injuries at two portions asymmetrically to the median line.

The ointments obtained in Examples 14–16 were applied to the rats from next day after the injury was induced in an amount of 0.2 g/injured region (as acetylsalicylic acid, 4 mg/injured region, 8 mg/injured region, or 16 mg/injured region), once a day for 14 days.

The therapeutic effects were evaluated by measuring the size in both of long and short diameters of the injured region to calculate the area. In the same manner as in Experiment 1, a curve of the change of area was drawn and the area below the curve was calculated. In the reference, the ointment base ("Plastibase") alone was applied.

Figure 5:
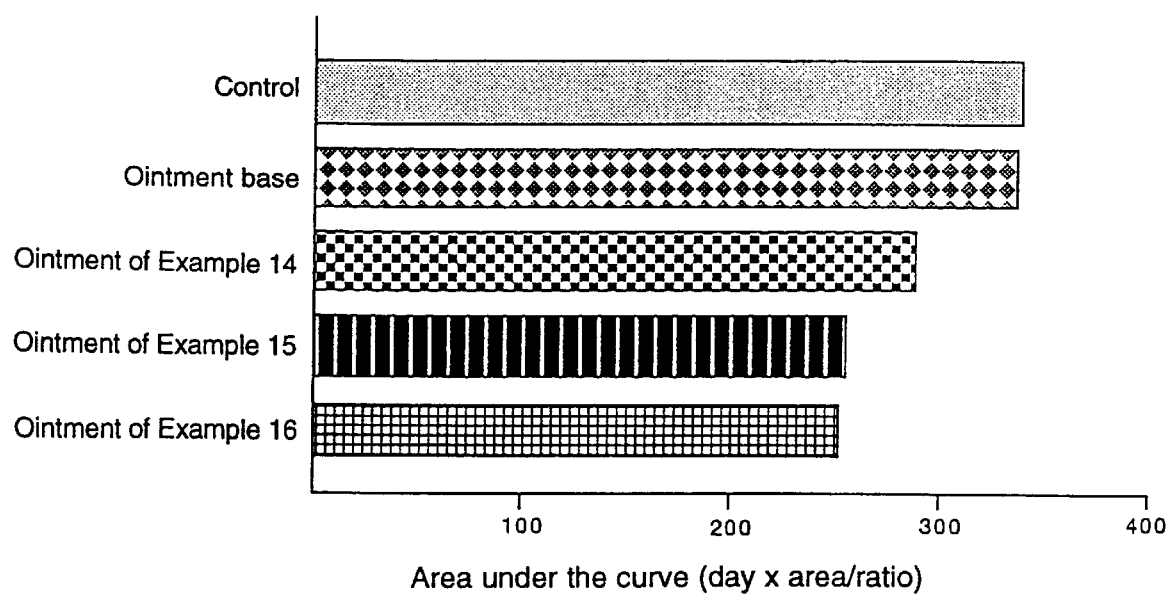
FIG. 5 shows a graph exhibiting therapeutic effects of acetylsalicylic acid when topically applied to a rat experimental skin-deficient model.

The results are shown in FIG. 5. As is clear from FIG. 5, the ointments containing acetylsalicylic acid of 2% by weight, 4% by weight and 8% by weight showed remarkable therapeutic effects.

As is clear from the above experimental results, the drug of the present invention is effective for various skin injuries including the hardly curable bedsore and further the ambustion, skin-deficient injuries.

What is claimed is:

1. A method for the treatment of a bedsore in a patient having a bedsore by promoting the formation of granulation tissue or epidermal tissue, which comprises topically applying an effective amount of an acetylsalicylic acid preparation to said bedsore.

2. The method according to claim 1, wherein the topical preparation is an ointment.

3. The method according to claim 1, wherein the topical preparation is a plaster.

4. The method according to claim 1, wherein the topical preparation is a gel.

5. The method according to claim 1, wherein the topical preparation is a cream.

6. The method according to claim 1, wherein the topical preparation is a powder.

7. The method according to claim 1, wherein the topical preparation is a topical solution.

8. The method according to claim 1, wherein the topical preparation contains acetylsalicylic acid in an amount of 0.05 to 15% by weight based on the whole weight of the topical preparation.

* * * * *